United States Patent
Surampudi

(10) Patent No.: US 11,169,104 B2
(45) Date of Patent: Nov. 9, 2021

(54) SIMULATING USE AND AGING OF IMMERSIVE COOLANTS FOR ELECTRIC MOTORS

(71) Applicant: Southwest Research Institute, San Antonio, TX (US)

(72) Inventor: Bapiraju Surampudi, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 84 days.

(21) Appl. No.: 16/746,317

(22) Filed: Jan. 17, 2020

(65) Prior Publication Data

US 2021/0223195 A1  Jul. 22, 2021

(51) Int. Cl.
| | |
|---|---|
| *G01N 27/02* | (2006.01) |
| *G01N 33/30* | (2006.01) |
| *G01N 11/00* | (2006.01) |
| *G01K 13/00* | (2021.01) |
| *G01N 33/28* | (2006.01) |

(52) U.S. Cl.
CPC .......... *G01N 27/023* (2013.01); *G01K 13/00* (2013.01); *G01N 11/00* (2013.01); *G01N 33/2888* (2013.01)

(58) Field of Classification Search
CPC .... G01N 27/023; G01N 27/025; G01N 33/28; G01N 33/2888; G01N 33/30; G01N 2011/006; G01N 2011/0066; G01N 2011/0086
See application file for complete search history.

(56) References Cited

U.S. PATENT DOCUMENTS

| 3,510,761 A | * | 5/1970 | Brown | G01N 27/023 324/445 |
| 5,091,704 A | * | 2/1992 | Kopera | G01N 27/023 123/575 |
| 5,659,251 A | * | 8/1997 | Wakamatsu | G01N 27/023 324/204 |
| 6,511,851 B1 | * | 1/2003 | Payne | G01N 27/023 436/149 |
| 2018/0106743 A1 | * | 4/2018 | Vogt | G01N 27/08 |
| 2019/0369053 A1 | * | 12/2019 | Winecki | G01F 23/263 |

FOREIGN PATENT DOCUMENTS

| JP | 2002 116185 A | 4/2002 |
| WO | WO 93/14394 A1 | 7/1993 |

* cited by examiner

*Primary Examiner* — Herbert K Roberts
(74) *Attorney, Agent, or Firm* — Livingston Law Firm

(57) ABSTRACT

A system for simulating the effects of use and aging on immersive coolants. Two conductive coils are immersed in a tank containing a sample of the coolant. The coils are spaced such that electrical activation of the first coil induces current in the second coil. A DC power source is provided to an inverter, which provides AC current for activating the first coil. The induced AC current in the second coil is delivered to a rectifier which converts the induced AC current to DC current. The DC current is then returned to the power source. The electromagnetic field between the coils simulates motor operation, so that the coolant's physical and chemical characteristics can be tested for the effects of use and aging.

8 Claims, 1 Drawing Sheet

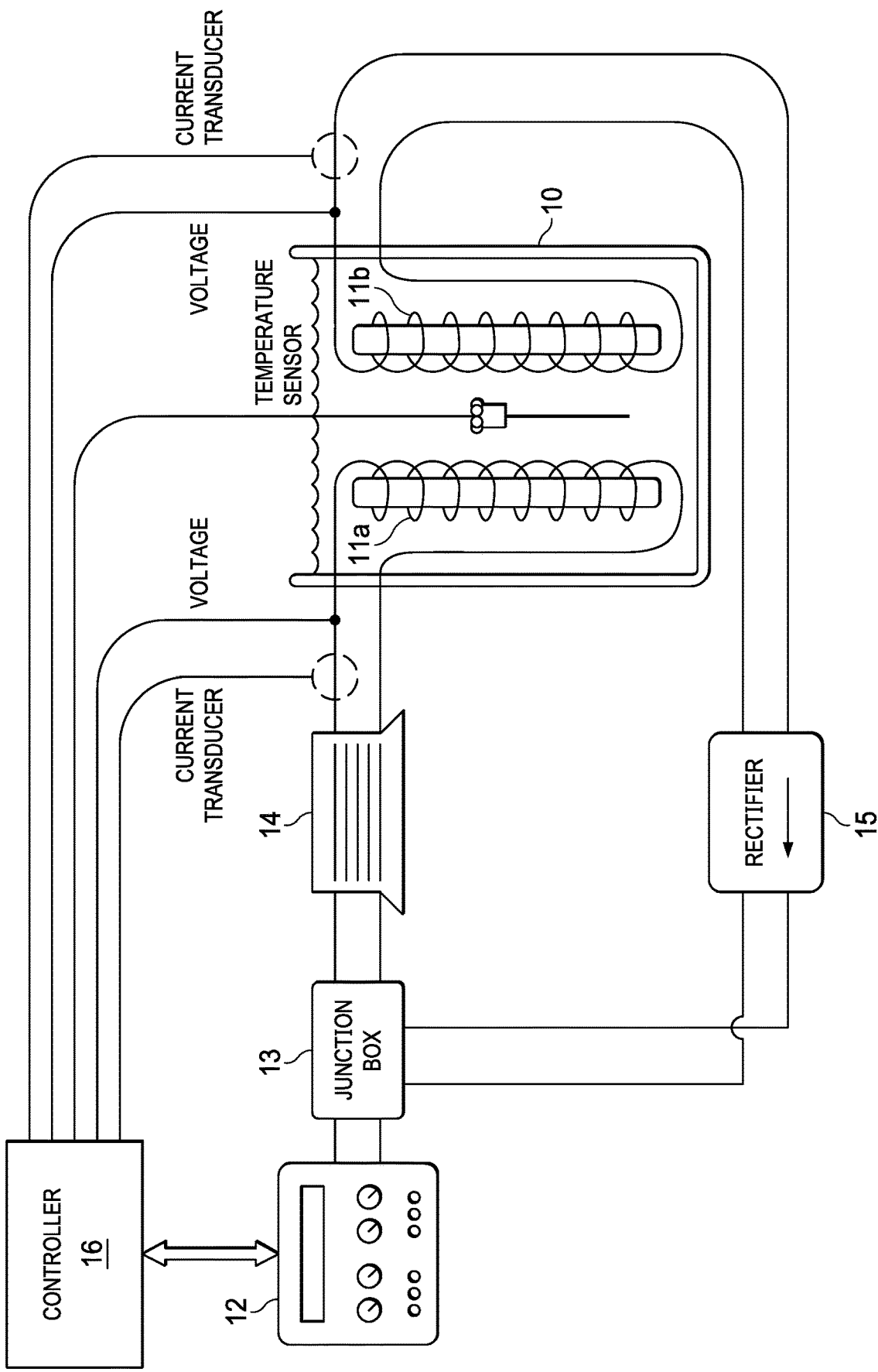

SIMULATING USE AND AGING OF IMMERSIVE COOLANTS FOR ELECTRIC MOTORS

TECHNICAL FIELD OF THE INVENTION

This invention relates to testing immersive coolants for electric motors, and more particularly to simulating motor dynamics for effects on such coolants.

BACKGROUND OF THE INVENTION

Hybrid and battery electric vehicles are rapidly increasing in popularity for both light duty and heavy duty applications. There is a strong need for the electric motors in these vehicles to be compact and capable of delivering high power.

A concern with these electric motors is high internal temperatures, especially near the motor windings, which can spike up sharply. Some sort of cooling is needed to transfer heat away from the motor.

One approach to cooling electric motors is immersive cooling. Immersive cooling with an engineered dielectric coolant delivers far greater heat transfer efficiency, allowing motors to be designed with smaller size and for use at higher temperatures. These coolants may also have enhanced lubricity to extend the life of motor and pump bearings.

A problem with immersive cooling for electric motors is premature failure of the coolant. It is believed that electromagnetic field effects from the motor result in reduced viscosity over time.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein:

FIG. 1 illustrates a test system for testing immersive coolants in accordance with the invention.

DETAILED DESCRIPTION OF THE INVENTION

The following description is directed to testing immersive coolants for electric motors. By "immersive coolant" is meant that at least some parts of the motor are immersed in a liquid that provides a coolant and/or lubricative function. Typically, the immersed parts are the internals of the stator and parts of the rotor.

Immersive coolants provide a non-electrically conductive (dielectric) heat transfer fluid. The heat transfer may result from passive circulation from natural convection of the coolant or from active circulation by pumping the dielectric coolant around the motor windings and then transferring absorbed heat to a radiator or other heat rejection device.

Often, immersive coolants for electric motors are also designed to provide extra lubrication, such as oil-based coolants. Because the coolant must combine a high flashpoint with high dielectric strength, an immersive coolant medium may also be referred to as an "insulating oil" or a "lubricative coolant". The test system and method described herein may be used to test any liquid in which a motor's internals are immersed, and such liquids are referred to herein collectively as "coolants".

FIG. 1 illustrates an immersive coolant test system 100 in accordance with the invention. As explained below test system 100 subjects a coolant to high frequency switching electromagnetic fields, thereby simulating the use of the coolant with an electric motor. The coolant can then be tested, in-situ or ex-situ, to determine various characteristics of the coolant. The test system 100 can test both the immediate condition of the coolant, as well as its degradation and aging over time.

As is known, an electric motor produces rotation of its rotor from a repeated sequence of attraction followed by repulsion, which requires reversing polarity. As an external power source passes through the rotor field, it serves as an electromagnet that is attracted to the permanent magnet of the stator. For continued rotation, the electromagnet allows the rotor field to reverse the polarity of its magnetic field producing repulsion. The repulsive force between the poles repels the electromagnet along its path of motion.

These switching magnetic fields are emulated by test system 100. Thus, test system 100 is useful for testing immersive coolants used with any electric motor that operates with switching electromagnetic fields. Typically, such motors can be referred to as "coil-based" motors.

In operation, a sample of an immersive coolant to be tested is contained in a tank 10. Two coils 11a and 11b are immersed in the coolant. Each coil 11a and 11b comprises electrical windings wrapped around a core.

Coils 11a and 11b are designed to imitate motor winding patterns. The type of winding can be varied to best imitate the motor(s) with which a coolant of interest will be used. The distance between coils 11a and 11b can be varied to emulate distances between actual motor windings, and to match various motor sizes and types.

A DC (direct current) power source 12 provides DC power for test system 100. DC power source 12 is programmable, delivering a desired level of power, typically within a range of 0 to 300 kW.

As explained below, the DC power from source 12 is recirculated through junction box 13. This minimizes power consumed by test system 100. An example of a suitable range of voltage from junction box 13 is 0-700 volts A first electrical path delivers current from junction box 13 to inverter 14, which converts the DC current to AC (alternating current) current. An example of a suitable range of outputs of inverter 14 is 0-480 Volts RMS with switching frequencies up to 30 kHz. This AC current is delivered to coil 11a.

The switching electromagnetic field from coil 11a is transferred inductively to coil 11b. As this switching occurs, the coolant is subjected to both electromagnetic and heat stress.

The induced current in coil 11b is delivered to rectifier 15, which converts the AC current to DC current. This current is fed back to junction box 13.

Because of this re-use of current induced in coil 11b, test system 100 is regenerative, generating minimal heat and consuming minimal power. It can be used as a universal test system for immersive coolants for electrical motors, with the electromagnetic field frequency and amplitude being variable to match any electric motor.

A controller 16 controls DC power supply 12 and the frequency of current provided by inverter 14. Controller 16 also acquires response signals from the coils and from a temperature sensor as indicated in FIG. 1. It converts these signals to current, voltage and temperature measurement data.

Controller 16 can be appropriately programmed to perform various tests on the coolant in-situ. For example, temperature and voltage variations can indicate changes in conductivity of the coolant. Alternatively, samples of the coolant can be removed and tested ex-situ.

Various metrics representing the condition of the coolant can be measured. One example of such a metric is dielectric breakdown voltage. Other coolant state of health metrics that can be indicated by appropriate measurement data are viscosity, change in coolant temperature as a function of number of hours of cycling, and change in the chemical composition of the coolant from extracted samples at various stages of cycling.

The test system 100 can be operated over time for a coolant of interest, thereby testing how the coolant's thermal performance and physical/chemical characteristics are affected by aging.

In some embodiments, it may be desired to use more than two coils. For example, aging effects or fluid breakdown due to electromagnetic fields can be accelerated with multiple coils. Also, the number of coils can match the number of windings in the stator to emulate distributed fields more closely.

What is claimed is:

1. A test system for testing immersive coolants used for electric motors, comprising:
    a tank for containing a sample of the coolant;
    at least two coils positioned within the tank such that they will be immersed in the coolant when the tank contains coolant;
    wherein a first coil is electrically connected to a first test path;
    wherein a second coil is electrically connected to a second test path;
    wherein the first coil and the second coil are arranged to imitate coils of an electric motor of interest and are spaced at predetermined distance such that electrical activation of the first coil induces current in the second coil; a DC (direct current) power source;
    a junction electrically connected to the power source, operable to deliver DC current to the first path, and to receive DC current from the second path;
    an inverter electrically connected on the first path between the junction and the first coil, operable to convert DC current to AC current for activating the first coil; and
    a rectifier electrically connected on the second path between the junction and the second coil, operable to convert induced AC current from the second coil to DC current.

2. A method of simulating the effect of electric motors on immersive coolants, comprising:
    placing a sample of the coolant in a tank;
    immersing at least two conductive coils in the tank;
    wherein a first coil is electrically connected to a first test path; wherein a second coil is electrically connected to a second test path;
    wherein the first coil and the second coil are arranged to imitate coils of an electric motor of interest and are spaced at predetermined distance such that electrical activation of the first coil induces current in the second coil;
    providing DC current from a DC power source to an inverter, which converts the DC current to AC current for activating the first coil;
    using a rectifier to convert induced AC current from the second coil to DC current; and
    delivering the DC current from the rectifier back to the DC power source.

3. The method of claim 2 further comprising selecting the frequency and amplitude of the AC current produced by the inverter to match the operation of a selected motor.

4. A method of testing immersive coolants used for electric motors, comprising:
    placing a sample of the coolant in a tank;
    immersing at least two conductive coils in the tank;
    wherein a first coil is electrically connected to a first test path; wherein a second coil is electrically connected to a second test path;
    wherein the first coil and the second coil are arranged to imitate coils of an electric motor of interest and are spaced at predetermined distance such that electrical activation of the first coil induces current in the second coil;
    providing DC current from a DC power source to an inverter, which converts the DC current to AC current for activating the first coil;
    using a rectifier to convert induced AC current from the second coil to DC current;
    delivering the DC current from the rectifier back to the DC power source;
    receiving electrical output signals from the first coil and the second coil; and
    analyzing the output signals to determine at least one physical or chemical property of the coolant.

5. The method of claim 4 further comprising selecting the frequency and amplitude of the AC current produced by the inverter to match the operation of a selected motor.

6. The method of claim 4 wherein the output signals are analyzed to determine viscosity of the coolant.

7. The method of claim 4 wherein the output signals are analyzed to determine dielectric breakdown voltage of the coolant.

8. The method of claim 4 further comprising measuring the temperature of the coolant over time during activation of the first coil and the second coil.

\* \* \* \* \*